United States Patent [19]

Ikeda

[11] 4,182,191
[45] Jan. 8, 1980

[54] METHOD OF IMMEDIATE ESTIMATION OF COMPRESSIVE STRENGTH OF CONCRETE THROUGH QUICK HARDENING

[76] Inventor: Shoji Ikeda, 5-4-11, Yayoi-cho, Nakano-ku, Tokyo, Japan

[21] Appl. No.: 940,015

[22] Filed: Sep. 6, 1978

[51] Int. Cl.² ............................................. G01N 3/08
[52] U.S. Cl. .................................................... 73/803
[58] Field of Search .................... 73/803, 432 R, 818, 73/821, 15.6

[56] References Cited

U.S. PATENT DOCUMENTS 3,974,679  8/1976  Nasser ................................. 73/803 X Primary Examiner—Jerry W. Myracle

[57] ABSTRACT

Immediate estimation of compressive strength of concrete at the standard curing age of concrete of 28 days being not affected by the weathering of cement used in the concrete is carried out by the addition of an alkali hydroxide as well as a setting accelerator to the mortar portion obtained by wet screening of fresh concrete.

6 Claims, 7 Drawing Figures

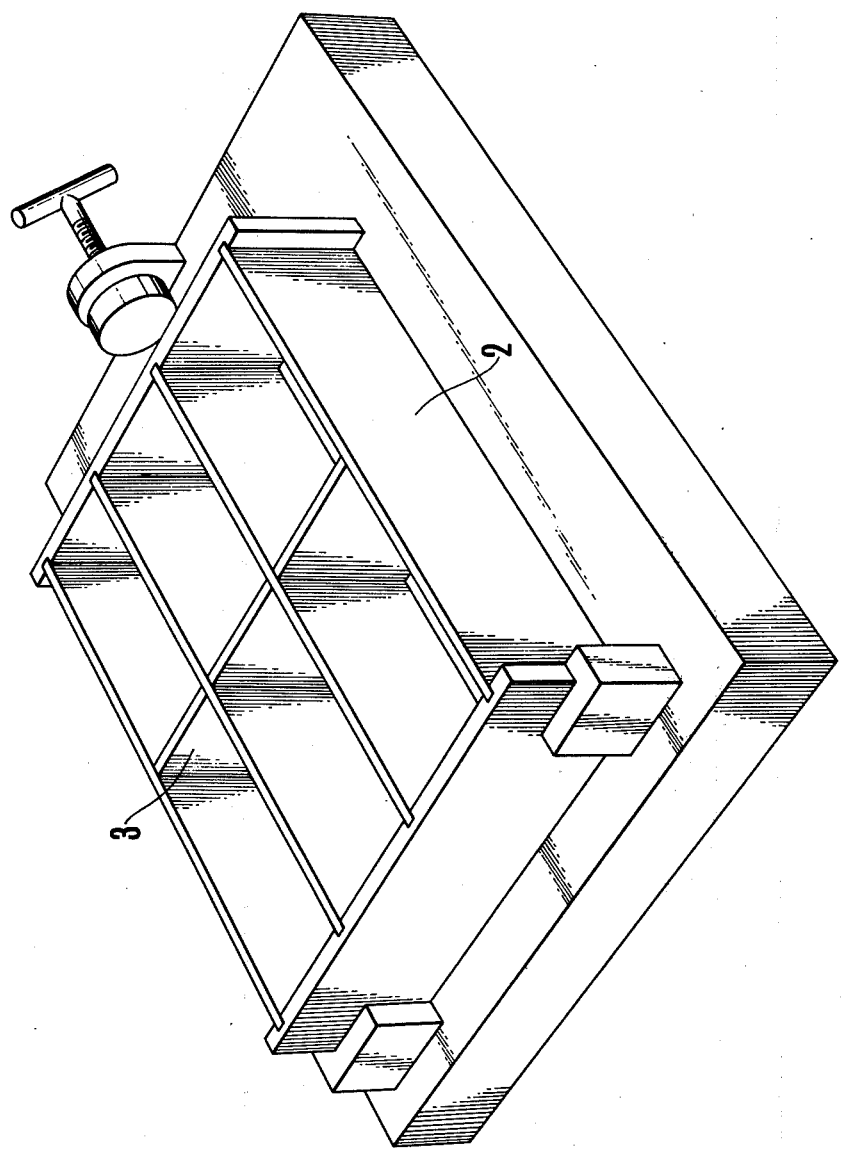

(1.5-HR CURING)

(3.0-HR CURING)

METHOD OF IMMEDIATE ESTIMATION OF COMPRESSIVE STRENGTH OF CONCRETE THROUGH QUICK HARDENING

This invention relates to a method of testing for estimation with good precision compressive strength of concrete at the standard curing age of 28 days, the standard value of compressive strength, a property representative of hardened properties of concrete, within a short period of time after completion of mixing of concrete.

The object of the present invention is to furnish a means of effectively performing quality control of concrete. The essential point in the constituent of this invention is the addition of a setting accelerator and alkali hydroxide to the mortar portion obtained by wet screening of fresh concrete for mixing followed by short-time, high-temperature curing. The combination of the addition of the alkali hydroxide as well as the setting accelerator and high-temperature curing will make possible estimation within a short period of time the compressive strength of concrete at the standard age of concrete of 28 days, while further, the addition of alkali hydroxide will reduce the influence on estimation results of the degree of weathering of cement used in the concrete to imrpove the accuracy of the estimation results and simultaneously indicate an effect of shortening the required high-temperature curing time.

The compressive strength of concrete is an extremely important physical characteristic representative of the hardened properties of concrete, which can indicate a different value depending on curing conditions and age even with the same concrete. Accordingly, the compressive strength at the standard curing age of 28 days is adopted as the standard value of compressive strength. In order to provide control of whether or not concrete used in concrete construction satisfies the required compressive strength level, compressive strength quality control tests of concrete are performed during concrete construcion work. Such tests are conducted collecting concrete samples from concrete finished mixing to make specimens, standard-curing these specimens, and subjecting these specimens to compressive strength tests when 28 days have elapsed after mixing of the concrete. The time at which compressive strength for the standard curing age of 28 days becomes known is after 28 days have elapsed from mixing of the concrete, during which time concrete work will have progressed substantially, and even in the event the test results obtained are unsatisfactory, it will not be possible to take any remedial steps. This has been a serious problem in the past in carrying out compressive strength quality control tests of concrete.

In order to resolve this problematic point, a number of methods for "early estimation of compressive strength of concrete" by which the compressive strength at standard curing age of 28 days could be estimated within a period of time as short as possible after completion of mixing of concrete has been proposed. Such an early-estimation method must satisfy the following 3 points to be suitable as a control test method in quality control of concrete. In effect, (1) The test results must be determined within a period of time as short as possible after mixing of concrete has been finished. In order for test results to be reflected in concrete construction work, it is desirable for the results to be known before the concrete mixed has been placed (within approximately 1 hour after mixing), or within a period of time of easy removal even after placement (period up to initiate of setting concrete, before approximately 5 hours after mixing).

(2) Fluctuation in test results must be small, with high reliability.

(3) Tests must be easily and economically carried out.

Of the "methods for early estimation of compressive strength of concrete" presently proposed, those representative are the two of "accelerated curing by heating method" and "rapid analysis method". The accelerated curing by heating method is a testing method for estimation compressive strength at the standard curing age of 28 days of the original concrete from the results of compressive strength tests on specimens made by taking samples from the concrete when mixing is finished and subjecting these specimens to accelerated curing by heating under curing conditions similar to steam curing. This method is not especially unsatisfactory with respect to the points (2) and (3) of the 3 points mentioned above, but since one day is required for test results to become known, there is much dissatisfaction regarding point (1) above. In the rapid analysis method, a sample of fresh concrete taken from concrete finished mixing is subjected to mix proportion analysis using an exclusive, specially designed analysis apparatus, computing the water-cement ratio of the concrete from the analysis results of unit cement content and unit water content obtained to estimate the compressive strength for the standard curing age of 28 days which is closely related to water-cement ratio. The time required for testing under this method is about one hour to satisfy (1) of the abovementioned 3 points, but since there are numerous factors to cause scatter in analysis results and the testing apparatus is generally expensive, there is much dissatisfaction with regard to points (2) and (3).

Thus, "method for early estimation of compressive strength of concrete" heretofore proposed although satisfying certain of the abovementioned conditions (1) to (3) which should be met for adoption as quality control tests for concrete, did not satisfy all of the conditions. The inventor, as a result of various studies to present a "method of early estimation of compressive strength of concrete" satisfying all of the abovementioned conditions (1) to (3), had proposed a "method of immediate estimation of compressive strength of concrete through quick hardening" essentially consisting of estimation compressive strength of the original concrete at the standard curing age of 28 days from the compressive strength of specimens made adding a setting accelerator to the mortar portion of fresh concrete obtained by wet screening and cured at high temperature. Details of this method were published by the inventor in Proceedings of Japan Society of Civil Engineers, No. 255, November 1976, pp. 103–112 under the title "Studies on a Method of Immediate Estimation of Concrete Strength Using Quick Hardening Process." Furthermore, the inventor published a paper entitled "Method of Immediate Estimation of Concrete Strength Using Quick Hardening Process" in Cement and Concrete, No. 316, August 1977. Still further, the inventor filed an application for a patent on the invention consisting of this technique (Japanese Pat. Appl. No. 51-54282, May 14, 1976.) However, it was found that with this immediate estimation method the estimation results are considerably influence by the degree of weathering of the cement used for the concrete, and as a result of various studies made to offset the influence of the degree of weathering of cement to improve the reliability of the estimation method, the problem was solved through the extremely simple means of joint use of an alkali hydroxide in addition to the setting accelerator, the result of which is the presentation of this invention. The inventor has published a paper entitled "Studies toward a Practical Use of the Method of Immediate Estimation of Concrete Strength" in Proceedings of Japan Society of Civil Engineers, No. 266, October 1977, pp. 123–134, which touches upon the technique of joint use of a setting accelerator and an alkali hydroxide.

An object of this invention is to provide a test method for estimation the standard-cured 28-day compressive strength of a concrete within a short period of time of 1 to 4 hours after completion of mixing of the concrete. Another object of this invention is to offset the influence of the degree of weathering of cement on the estimation results of the previously-mentioned test method to improve the reliability of the estimation results of the said test method.

Other objects and advantages of this invention will be apparent from the attached drawings wherein:

FIG. 2 is an oblique pictorial drawing of an example of a mold for manufacturing specimens;

Figure 1:
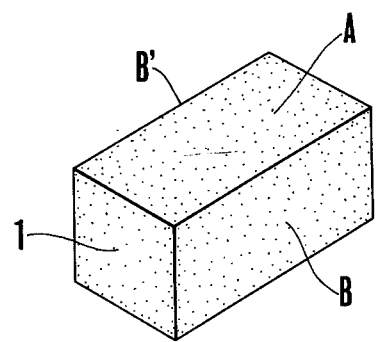
FIG. 1 is an oblique pictorial drawing of a specimen.

The method of immediate estimation of compressive strength of concrete through qucik-hardening of this invention comprises the procedures (i) through (vi) below.

(i) Concrete sample taken from fresh concrete for which mixing has been completed is subjected to wet screening using a 5-millimeter sieve to remove the coarse aggregate portion of the concrete and obtain the mortar portion.

(ii) A setting accelerator and an alkali hydroxide are added to the mortar portion obtained by the preceding procedure (i) and mixing is performed. The setting accelerator may be an alkali aluminate or an alkali carbonate, or a mixture of the two, mixtures of alkali aluminate and alkali carbonate at ratios by weight of 1:1 to 1:5 being desirable. The rate of addition of setting accelerator is 2 to 8 percent by weight of the cement contained in the mortar portion. The rate of addition of alkali hydroxide is 0.5 to 3 percent by weight of cement contained in the mortar, and moreover, 10 to 50 percent by weight of the setting accelerator.

(iii) The mortar portion to which setting accelerator and alkali hydroxide has been added according to the preceding procedure (ii), on mixing is cast in molds for forming rectangular parallelepiped specimens to make specimens.

(iv) Specimens made according to the preceding procedure (iii) are placed in a high-temperature curing chamber in a condition while still filled in the molds, said chamber maintained at constant temperature and roughly saturated humidity for said temperature, and high-temperature curing is done for the specified period of time. The temperature and length of time of high-temperature curing is a suitable combination of temperature and time selected from a temperature range of 60 to 90 degrees centigrade and a time range of 0.5 to 4 hours.

(v) On completion of the high-temperature curing according to the preceding procedure (iv), the mold is removed from the high-temperature curing chamber, the specimens contained inside are removed, and compressive strength tests are performed on these specimens.

(vi) The compressive strength of the mortar portion obtained through the preceding procedures (i) through (v) and the compressive strength of the original concrete at the standard curing age of 28 days are closely associated with each other, and utilizing the relation between the two, the compressive strength at 28 days of standard curing of the original concrete is estimated from the compressive strength of the mortar portion obtained by the preceding procedures (i) through (v).

More detailed descriptions of the abovementioned procedures will next be given. Wet screening is performed to separate the coarse aggregate and mortar portions (components other than the coarse aggregate—mixture of cement, water, fine aggregate, etc.) of fresh concrete. For this purpose, the sieve used for wet screening possesses openings of 5 millimeters, the borderline differentiating between coarse and fine aggregates. Sieves suitable for this purpose may be cited as the 5-millimeter sieve specified in JIS Z 8801 (Sieves for Testing Purposes), U.S. standard No. 4 sieves, or equivalent sieves.

Accelerating compressive strength gain performing high-temperature curing adding setting accelerator (and alkali hydroxide) is herein termed quick hardening, and the relation between compressive strength of quick-hardened mortar and quantity of addition of setting accelerator was that of increase with addition up to approximately 3 percent by weight of cement contained in the mortar portion, more or less constant value between approximately 3 to 6 percent by weight, a trend rather for decrease above 6 percent by weight, and beyond 8 percent by weight loss of all significance of addition. Furthermore, when the addition rate of setting accelerator is less than 2 percent by weight, the quick-hardening effect will be insufficient.

The effect of offsetting the influence of the degree of weathering of cement by addition of alkali hydroxide is insufficient at below 0.5 percent by weight of cement, while the effect is not especially increased on addition of 3.0 percent or more by weight. The effect of addition if alkali hydroxide is insufficient when the ratio of the alkali hydroxide to setting accelerator is less than 10 percent by weight, while there is no special increase at 50 percent or more by weight, and considering various circumstances 15 to 30 percent by weight will be suitable.

The quantity of cement contained in the mortar portion obtained by wet screening may be determined by calculations assuming that all components other than coarse aggregate in the concrete mix proportions are included in the mortar portion. In concrete of ordinary mix proportions, since the proportion of cement contained in the mortar portion is more or less in a constant range, when setting accelerator is added 1 percent by weight with weight of the mortar portion as a basis, this will correspond to at least 3 percent by weight or more to cement. This addition quantity, as described above, is in a range of addition where compressive strength of quick-hardened mortar is subjected to almost no effect, and when carrying out the previously-mentioned procedure (ii), it will be permissible for setting accelerator to be added at a uniform rate of 1 percent by weight to the mortar portion even if the mix proportion of concrete were to vary in many ways.

When adding setting accelerator and alkali hydroxide to the mortar portion, they may be added separately according to their specified quantities, or a mixture of the two made beforehand may be added. The desirable form of execution of procedure (ii) is for a mixture of alkali hydroxide and setting accelerator at a ratio by weight of 1:4 to 1:5 to be added in a proportion that addition of the setting accelerator will be 1 percent by weight of the mortar, or the setting accelerator will be 4 percent by weight of the cement contained in the mortar portion.

The specimens used for this invention are of rectangular parallelepiped shape as indicated in FIG. 1, the dimensions of the various parts not being especially limited, but it will be desirable for the specimen to be as small as possible. An example of a mold for manufacturing the rectangular parallelepiped specimens is shown. The mold 2 indicated in FIG. 2 is a triple gang mold for making cement strength test specimens (4×4×16 centimeters) specified in JIS R 5201 provided with a partitioning board 3 at the middle with which a maximum of 6 rectangular parallelpiped specimens of 4×4×7.5 centimeters can be made. Further, if rectangular parallelepiped specimens of $\sqrt{10} \times \sqrt{10} \times 5$ centimeters are used, they will be smaller than the abovementioned specimens of 4×4×7.5 centimeters, allowing a smaller quantity of sample to be used, in addition to which it will be convenient in performing compressive strength tests as described later. When specimens of $\sqrt{10} \times \sqrt{10} \times 5$ centimeters are used, existing molds cannot be utilized unlike cases of specimens of 4×4×7.5 centimeters, and therefore, specially made molds are used. In making specimens, molds are filled in two layers and consolidation by tamping is to be thoroughly performed.

The compressive strength of quick-hardened mortar increases rapidly after starting of high-temperature curing, but the increase eventually slows down, and in the end the strength becomes roughly constant. Selection of the high-temperature curing conditions should be with conditions under which compressive strength of quick-hardened mortar will be stabilized as stated above as the criteria, and the minimum curing time may be made 3 hours at 60° C., 1 hour at 70° C., and 0.75 hours (45 minutes) at 80° C., but it will be desirable for the minimum curing times for practical purposes to be the abovementioned times respectively prolonged by 0.5 hour. Higher curing temperature will make it possible for the curing time required to be shortened, but for example, at high temperatures in excess of 80° C., there will be danger of workers suffering burns through blow-out of steam when the curing chamber is opened, and adequate protective means will become necessary.

Further, it is not a desirable thing for temperature-rise of a specimen to be overly rapid. Taking these circumstances into consideration, it will be desirable for the curing temperature to be 70° C. and curing time 1.0 to 3.0 hours (desirably, 1.5 hours).

Figure 3:
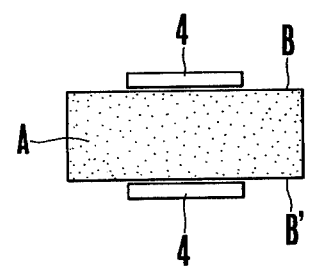
FIG. 3 is a side view of the form of a specimen when it is to be subjected to a compressive strength test.

The top surface A of a specimen (1 in FIG. 1) removed from the mold after completing high-temperature curing, is not in contact with a mold wall when cast so that it is not flat, and it will not be possible to use this surface as the loading surface when performing compressive strength tests unless the surface is made a flat plane by capping. In carrying out compressive strength tests the specimen 1 in FIG. 1 is to be rotated 90 degrees and positioned in a manner that surfaces B and B' which were side surfaces at time of molding will be used as the top and bottom surfaces. (Surfaces B and B' possess ample flatness for utilization as loading planes as they were in contact with surfaces of molds during casting.) Steel plates 4 of square shape are placed against the surfaces B and B' and compressive strength of the specimen 1 is measured applying load to the steel plates 4. The size of a steel plate 4 is to be 4×4 centimeters in case of a specimen of 4×4×7.5 centimeters and $\sqrt{10} \times \sqrt{10}$ centimeters in case of a specimen of $\sqrt{10} \times \sqrt{10} \times 5$ centimeters. The compressive strength (kilograms per square centimeter) of a specimen may be determined by dividing the total load applied (kilogram) by the area (square centimeters) of a steel plate 4, and in case a specimen of $\sqrt{10} \times \sqrt{10} \times 5$ centimeters is used the area of a steel plate 4 will be exactly 10 square centimeters and convenient for calculation of compressive strength. End portions of specimens are liable to be chipped and become weak points. Accordingly, in performing compressive strength tests, the mode as indicated in FIG. 3 is to be followed in order to avoid these weak portions and only the middle part of uniform strength is used, and instead of cubes, rectangular parallelepipeds are therefore used as the specimens.

According to research conducted by the inventor the quick-hardened compressive strength ($\sigma_m$) of mortar obtained by wet screening has the relationship of the equation below with the cement-water ratio (c/w) of the original concrete:

$$\sigma_m = m_1 \cdot \frac{c}{w} + m_2 \qquad (1)$$

Meanwhile, it is well-known that the same relationship as Eq. (1) holds between compressive strength of concrete at standard-curing age of 28 days and c/w.

$$\sigma_{28} \cdot = k_1 \cdot \frac{c}{w} + k_2 \qquad (2)$$

Eliminating c/w from Eqs. (1) and (2), the following equation is obtained:

$$\sigma_{28} = \alpha \cdot \sigma_m + \beta \qquad (3)$$

provided that $$\alpha = \frac{k_1}{m_1} \qquad (4)$$

$$\beta = k_2 - \frac{k_1 m_2}{m_1} \qquad (5)$$

If, prior to estimation tests, the coefficients in the abovementioned Eq. (3) were to be determined beforehand, $\sigma_{28}$ may be estimated from $\sigma_m$ utilizing Eq. (3).

The most orthodox method of determining the coefficients in Eq. (3) would be to mix concretes of varying c/w using identical materials as for the concrete for which estimation tests are intended to actually obtain $\sigma_m$ and $\sigma_{28}$ and determine these coefficients from actual measurements in advance. However, it is necessary for $\sigma_{28}$ to be determined with this orthodox method and tests to obtain the coefficients in Eq. (3) (hereinafter called preliminary tests) must be conducted at least 28 days before the estimation tests are to be carried out.

With respect to the coefficients $k_1$ and $k_2$ in the abovementioned Eq. (2), more or less appropriate values have been proposed upon arrangement of data obtained on concrete in the past, and these may be utilized. Accordingly, there is also a method of preliminary test where concretes of mix proportions of varying c/w are mixed using materials identical to those of the concrete intended to be tested, only $\sigma_m$ is determined for mortar obtained by wet screening these concretes to find the coefficients in Eq. (1), adopting existing values for $k_1$ and $k_2$, and obtaining the coefficients $\alpha$ and $\beta$ throgh calculations by Eqs. (4) and (5). In such case, the number of days required for the preliminary tests can be small (for example, 1 day would suffice) as $\sigma_{28}$ is not obtained.

Further, in preliminary tests, there is a method allowing the coefficients $\alpha$ and $\beta$ in the beforementioned Eq. (3) to be estimated mixing only mortar and not concrete. Mortars of mix proportions varying c/w are mixed using materials identical to those for the concrete intended to be tested, and the compressive strengths ($\sigma_{mo}$) when these are quick-hardened similarly to the case of Eq. (1) will have the relation of the following equation with c/w.

$$\sigma_{mo} = m_{01} \cdot \frac{c}{w} + m_{02}. \quad (6)$$

Meanwhile, it has been established in the inventor's research that the equation below will be valid between $\sigma_m$ and $\sigma_{mo}$.

$$\sigma_m = a_1 \sigma_{mo} + a_2 \quad (7)$$

Eliminating c/w and $\sigma_{mo}$ from Eqs. (2), (6) and (7), the following equation will result:

$$\sigma_{28} = \left(\frac{k_1}{a_1 \cdot m_{01}}\right) \sigma_m + \left(k_2 - \frac{a_1 \cdot m_{02} + a_2}{a_1 \cdot m_{01}} \cdot k_1\right) \quad (8)$$

On comparison with Eq. (3):

$$\alpha = \frac{k_1}{a_1 \cdot m_{01}} \quad (9)$$

$$\beta = k_2 - \frac{a_1 \cdot m_{02} + a_2}{a_1 \cdot m_{01}} \cdot k_1 \quad (10)$$

The coefficients $a_1$ and $a_2$ in the above Eq. (7) will vary to an extent depending on the variety of material and conditions of quick hardening, but are fairly stable coefficients and for practical purposes may be considered constant within the limits of materials of the same variety and similar quick-hardening conditions, it being possible for appropriate values to be proposed based on past experimental data. When $m_{01}$ and $m_{02}$ are known, estimated values may be employed for other coefficients and $\alpha$ and $\beta$ may be computed from Eqs. (9) and (10). Thus, in preliminary tests, it will suffice to mix only mortar without any concrete to simplify the preliminary tests still further.

The length of time required for executing the estimation method of this invention is the high-temperature curing time plus the time required for various operations, this latter time requirement being approximately 15 minutes.

The various observations made in executing the estimation method of this invention will next be cited.

(a) Effect of precuring period. With ordinary concrete the time from mixing of concrete until placement will vary considerably due to circumstances at the job-site, and if the compressive strength of the quick-hardened mortar were to differ greatly depending on the time from completion of mixing of concrete until addition of setting accelerator, this would be an obstacle to practical use. As a result of examinations, it was found that there is practically no influence of the length of time from mixing of concrete until addition of setting accelerator within a range of 2 hours.

(b) It was found that there is practically no increase in compressive strength of quick-hardened mortar during the period left standing at room temperature after completion of high-temperature curing. Parenthetically, there will be no effect on tests results even though compressive strength tests are not performed immediately after completion of high-temperature curing.

(c) It was recognized that quick-setting and hardening characteristics differ depending on the type and brand of cement.

(d) In the event that the temperature of mortar before start of high-temperature curing differs, influence can be seen in case of starting high-temperature curing 30 minutes after addition of quick-setting agent, but if high-temperature curing is begun 5 minutes after addition of setting accelerator, practically no influence of this mortar temperature can be recognized.

(e) The coefficients in Eq. (3) hereinbefore mentioned will be subjected to practically no influence even though a retarding agent may be added to the concrete.

The advantages of the estimation method of this invention will next be enumerated.

(1) The length of time required from start of testing until completion is approximately 1 hour to 4 hours, extremely short compared with the time required in case of the early estimation methods using conventional accelerated curing. Accordingly, it will be possible to cause the test results to be reflected in the concrete work. This shortening of the required time is made possible by the combined employment of the two means of addition of setting accelerator and high-temperature curing. The compressive strength of mortar at the age of 4.5 hours in case setting accelerator is added but high-temperature curing is not performed is only 5.2 kilograms per centimeter, while the compressive strength of mortar without addition of setting accelerator but with only high-temperature (70° C.) curing done reaches only 17 kilograms per square centimeter at 3.0 hours of curing. (Ratio of cement and sand of mortar 1:2.67, water-cement ratio 0.60, setting accelerator 1 weight percent of mortar.) For the same mortar with equal amount of setting accelerator added and 1.5 hours of high-temperature at 70° C., the compressive strength was 55 kilograms per square centimeter.

(2) Through the combined use of alkali hydroxide with setting accelerator, it is possible to offset the influence of weathering of cement on the compressive strength of quick-hardened mortar to improve the reliability of the estimation test.

(3) In the event of addition of a mixture of setting accelerator and alkali hydroxide, compared with the case of addition of an equal amount of setting accelerator only, the compressive strength gain of quick-hardened mortar will become larger. Through this, it will become possible to further shorten the required high-temperature curing time compared with when setting accelerator alone is added.

(4) With the conventional early estimation method, specimens were made of concrete. (Specimens were cylindrical of dimensions of 10-centimeter diameter by 20 centimeters or 15-centimeter diameter by 30 centimeters.) With this invention, the merit lies in the fact that specimens are made with mortar. In effect, in case of mortar specimens, the sample collected will be sufficient with a far smaller quantity than in case of concrete, and since specimen-size is small, it will be adequate for the testing apparatus to be small as a whole, and execution of tests will become simple and economical.

(5) Further, since mortar specimens are of small size, it is easier for uniform temperature distribution to be obtained in heating, and it is possible for rapid temperature rise to be carried out. This is a characteristic which is particularly advantageous when attempting to shorten as much as possible the time of curing at high temperature as with the estimation method of this invention. In case of concrete specimens, uneven temperature distribution is liable to occur between the surface portion and interior so that rapid temperature rise cannot be effected, and the time required for high-temperature curing becomes long of necessity.

(6) In the past, cylindrical forms have been used as specimens for compressive strength tests. With such specimens, the top surfaces would not have been in contact with mold surfaces so that they were not flat and smooth and it was necessary to provide capping. If capping is to be done, it will not be possible to start compressive strength tests within a short period of time after molding of specimens. As rectangular parallelepiped specimens are used in this invention, it is not necessary for capping to be done as stated in connection with FIG. 3.

(7) When setting accelerator is added to concrete flowability will be rapidly lost so that in casting specimens with this concrete it is not possible for dense filling to be done. In case of removing coarse aggregate by wet screening, it will be possible for molds to be densely filled even when the flowability of the mortar is reduced due to addition of setting accelerator. In this point also, there is an advantage in making specimens with mortar and not concrete.

EXAMPLE 1

This example is a case of test indicating the effect of alkali hydroxide on offsetting the influence of the degree of weathering of cement.

(1) Method of testing. Mortar was mixed according to proportions of ratio by weight of cement to sand of 1.0:2.0, and water-cement ratio of 0.70, to which setting accelerator was added 3.7 weight percent to cement and sodium hydroxide or potassium hydroxide was added at the two levels of 0.5 weight percent and 1.0 weight percent to cement, hand-mixing was done for 1 minute, and this mortar was filled in molds as shown in FIG. 2 to make rectangular parallelepiped specimens of 4×4×7.5 centimeters. High-temperature curing was done at the two levels of 1.5 hours and 3.0 hours at 70° C. For comparison, tests in case of addition of setting accelerator only (3.7 weight percent of cement) were also conducted.

The setting accelerator used here was a mixture of 1:3 ratio by weight of sodium aluminate and sodium carbonate (hereinafter abbreviated as ACM).

The cement used was Asano Type I cement, and this was thinly spread out and left in a constant temperature room of 20° C. and 80 percent relative humidity to be weathered for 1 day and 2 days. It is estimated that the degree of weathering of cement actually used in concrete work corresponds to less than 1-day weathering under the abovementioned weathering conditions.

Figure 4:
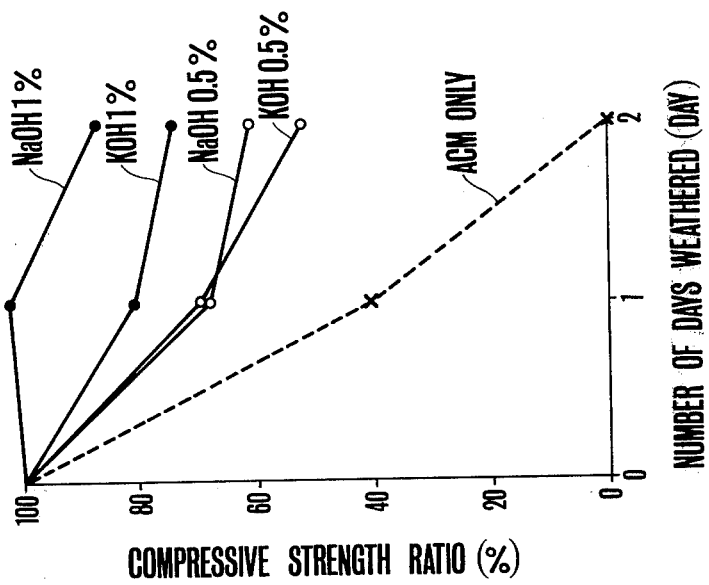
FIG. 4 illustrates the relation between compressive strength of quick-hardened mortar in case of 1.5 hours of high-temperature curing and the number of days of weathering of cement.
Figure 5:
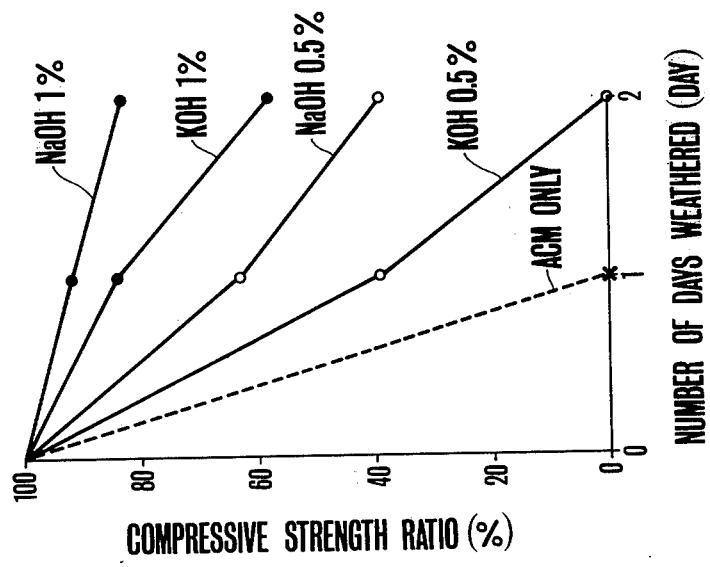
FIG. 5 illustrates the relation between compressive strength of quick-hardened mortar in case of 3.0 hours of high-temperature curing and the number of days of weathering of cement.

(2) The test results are indicated in FIG. 4 (high-temperature curing for 1.5 hours) and in FIG. 5 (high-temperature curing for 3.0 hours). In these figures are indicated the percentages of the compressive strengths of quick-hardened mortars when cements of various days of weathering were used to the compressive strength of quick-hardened mortar using cement of zero-days of weathering for each addition rate. Further, regarding the compressive strength of mortar at standard curing age of 28 days when setting accelerator and alkali hydroxide were not added, with the strength using cement of zero-day weathering as 100 percent, the case of 1-day weathering was 92 percent and the case of 2-day weathering 78 percent.

As is clear from the illustrations, the influence of weathering of cement is great in case of addition of setting accelerator only. However, when alkali hydroxide is used in combination, the effect of weathering of cement is offset.

EXAMPLE 2

This example is that of a test indicating the condition of compressive strength gain of quick-hardened mortar under high-temperature curing.

Figure 6:
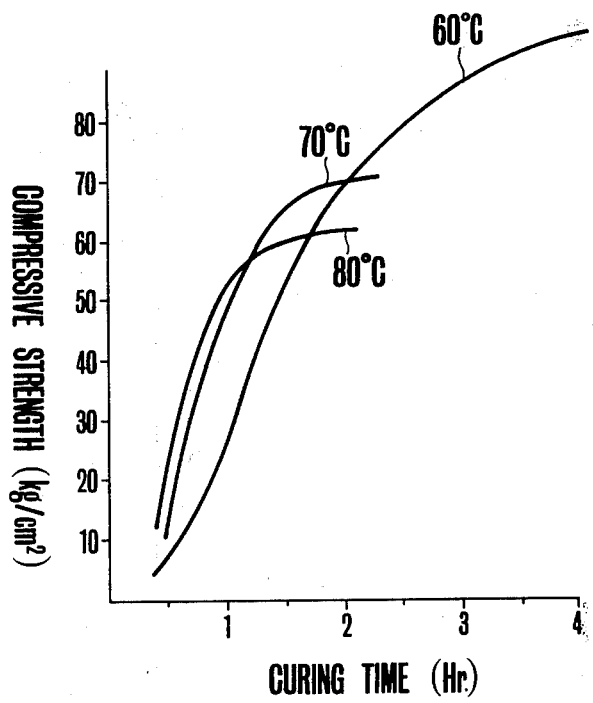
FIG. 6 illustrates the relations of high-temperature curing time-lengths at various high curing temperatures and compressive strengths of quick-hardened mortars.

Mortar of cement-sand ratio of 2.72, water-cement ratio of 0.556 was mixed and to this a mixture of the setting accelerator ACM used in Example 1 and sodium hydroxide at a ratio by weight of 5:1 was added at a rate of 1.2 weight percent of mortar weight. The specimen dimensions were $\sqrt{10} \times \sqrt{10} \times 5$ centimeters. The high-temperature curing levels were of the three of 60° C., 70° C. and 80° C., and the maximum curing time was 4.0 hours. The results are shown in FIG. 6. From this figure, it may be seen that the time at which compressive strength gain of quick-hardened mortar begins to become more or less stable is 3.0 hours at 60° C., 1.0 hour at 70° C., and 0.75 L hour at 80° C., but it can be seen that more stable conditions are obtained at times 0.5 hours longer than the respective lengths of time above.

EXAMPLE 3

This example will serve to show tests carried out on the estimation method of this invention for concretes of various mix proportions.

(1) Method of Testing

Type I portland cement, river sand and river gravel were used for the concrete, and for all mix proportions air-entraining type water-reducing admixtures were used for air entrainment at a level of approximately 4 to 5 percent. The concrete mix proportions were for 3 cement brands, 2 levels of slump at 9 centimeters and 18 centimeters, and 30 varieties of concrete mixes. Compressive strengths of quick-hardened mortars were measured in accordance with the procedures (i) through (v) previously mentioned.

The 4:1 by weight mixture of setting accelerator ACM and sodium hydroxide described in Example 1 was added at a rate of 1 weight percent of mortar and high-temperature curing was performed for 1.5 hours and 3.0 hours at 70° C.

Meanwhile, using identical materials as for the concrete above, mortar was mixed, and with quick-hardening provided under the same conditions as for the above, compressive strengths were measured. Also, tests were conducted for comparisons of the cases of addition of setting accelerator ACM only for this mortar.

(2) Test Results

The compressive strength $\sigma_m$ of quick-hardened mortar and the compressive strength $\sigma_{28}$ at the standard-curing age of 28 days of the original concrete were plotted on a graph, and the coefficients $\alpha$ and $\beta$ of the beforementioned Eq. (3) were determined by the method of least squares. The results obtained were the following:

$$\sigma_{28}=2.98\cdot\sigma_m+144 \text{ (kg/cm}^2\text{)[1.5-hr curing]} \quad (11)$$

$$\sigma_{28}=2.68\cdot\sigma_m+119 \text{ (kg/cm}^2\text{)[3.0-hr curing]} \quad (12)$$

The ratio of estimated values of $\sigma_{28}$ calculated from $\sigma_m$ using these estimation formulae for $\sigma_{28}$ to measured values of $\sigma_{28}$ for 30 varieties of concrete was taken. In case of 1.5 hours of curing the average value was 1.013 and standard deviation 0.107, and in case of 3.0 hours of curing the average value was 1.011 and the standard deviation 0.102. The 30 varieties of concrete mentioned above covered a wide scope with different cements and admixtures, but nevertheless, the accuracy of $\sigma_{28}$ estimation was more than satisfactory for this type of estimation method.

The coefficient of Eq. (7) previously mentioned assumed the values below.

$$\sigma_m=0.94\ \sigma_{mo}+6.9 \text{ (kg/cm}^2\text{)[1.5-hr curing]} \quad (13)$$

$$\sigma_m=0.88\ \sigma_{mo}+11.4 \text{ (kg/cm}^2\text{)[3.0-hr curing]} \quad (14)$$

Figure 7:
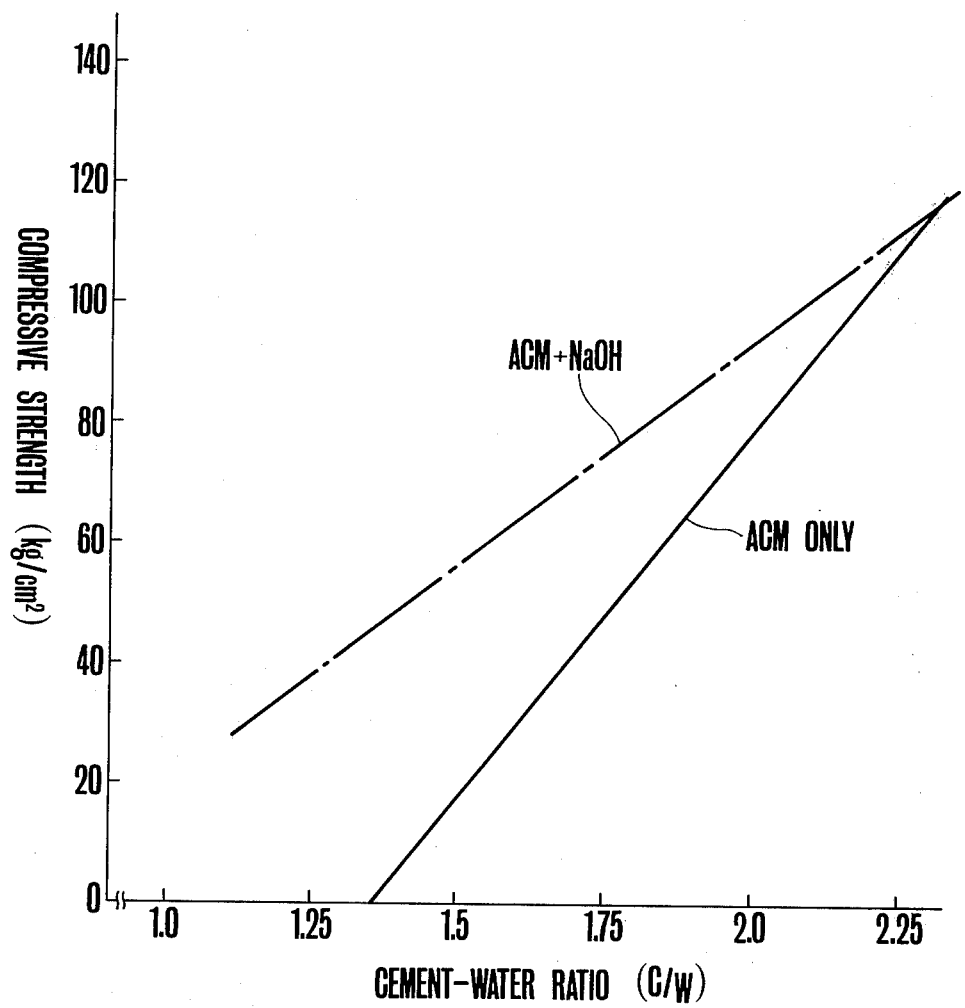
FIG. 7 illustrates the relation between the cement-water ratio (c/w) and compressive strength of quick-hardened mortar.

Next, the relations between compressive strength of quick-hardened mortar and the cement-water ratio (c/w) of the mortar, in case of addition of setting accelerator ACM only and in case of addition of a mixture of setting accelerator ACM and sodium hydroxide have been indicated in FIG. 7 (addition rate both being 1 weight percent of mortar).

As is distinctly shown in this figure, within a practical range of c/w, compressive strength gain is greater in case of combined addition of setting accelerator and alkali hydroxide than in case of addition of setting accelerator only.

What is claimed is:

1. A method of immediate estimation of compressive strength of concrete characterized by the compressive strength of concrete at the standard curing age of 28 days estimated accurately according to the steps (i) through (vi) hereinafter set forth within a short period of time from completion of mixing of concrete, said steps being:

(i) collection of the mortar portion of concrete through separation and removal of the coarse aggregate portion of concrete by wet screening with a 5-millimeter opening sieve from a concrete sample collected from fresh concrete for which the mixing has been finished;

(ii) adding a setting accelerator and an alkali hydroxide to the mortar portion collected by the preceeding step (1) and mixing thereof, the setting accelerator being an alkali aluminate, or an alkali carbonate, or a mixture of the two, the amount of addition of the setting accelerator being 2 to 8 weight percent of the cement contained in the mortor portion, the amount of addition of alkali hydroxide being 0.5 to 3 weight percent of the cement contained in the mortar portion, and 10 to 50 weight percent of the setting accelerator;

(iii) filling of the mortar portion to which setting accelerator and alkali hydroxide have been added and which has been mixed according to the preceeding step (ii) in molds for forming rectangular parallelepiped specimens to cast specimens;

(iv) placing the specimens made according to the preceeding step (iii) in a high-temperature curing chamber in a condition while still filled in the molds, said chamber being maintained at a constant temperature and roughly saturated humidity for said temperature, for high-temperature curing for the specified length of time, said temperature and length of time of high-temperature curing being a suitable combination of temperature and time selected from a temperature range of 60° to 90° C. and a time range of 0.5 to 4 hours;

(v) removal of the molds from the high-temperature curing chamber on completion of high-temperature curing according to the preceeding step (iv), removal of the specimens contained inside, and performing compressive strength tests on the specimens;

(vi) the compressive strength of the mortar portion obtained by the preceeding steps (i) through (v) and the compressive strength of the original concrete at the standard curing age of 28 days being closely associated with each other, estimation of the compressive strength at the standard curing age of 28 days of the original concrete from the compressive strength of the mortar portion obtained by the preceeding steps (i) through (v) by utilizing the relation between the two compressive strengths.

2. A method of immediate estimation of compressive strength of concrete by quick hardening characterized by the amount of addition of setting accelerator in claim 1 being 3.0 to 6.0 weight percent of the cement contained in the mortar portion, with moreover the amount of addition of alkali hydroxide being 15 to 30 weight percent of the amount of addition of the setting accelerator.

3. A method of immediate estimation of compressive strength of concrete by quick hardening characterized by the high-temperature curing in procedure (iv) according to claim 2 being 1.0 to 3.0 hours at 70° C.

4. A method of immediate estimation of compressive strength of concrete by quick hardening characterized by the setting accelerator in claim 3 being a mixture of an alkali aluminate and an alkali carbonate in the range of ratios by weight of 1:1 to 1:5.

5. A method of immediate estimation of compressive strength of concrete by quick hardening characterized by the setting accelerator in claim 2 being a mixture of an alkali aluminate and an alkali carbonate in the range of ratios by weight of 1:1 to 1:5.

6. A method of immediate estimation of compressive strength of concrete by quick hardening characterized by the setting accelerator in procedure (ii) of claim 1 being a mixture of an alkali aluminate and an alkali carbonate in the range of ratios by weight of 1:1 to 1:5.

* * * * *